United States Patent [19]

Merger et al.

[11] 4,384,120

[45] May 17, 1983

[54] PREPARATION OF PYRIDINES

[75] Inventors: Franz Merger, Frankenthal; Gerd Fouquet, Neustadt, both of Fed. Rep. of Germany

[73] Assignee: BASF Aktiengesellschaft, Ludwigshafen, Fed. Rep. of Germany

[21] Appl. No.: 339,998

[22] Filed: Jan. 18, 1982

[30] Foreign Application Priority Data

Jan. 30, 1981 [DE] Fed. Rep. of Germany ....... 3103108

[51] Int. Cl.$^3$ .......................................... C07D 213/14
[52] U.S. Cl. ..................................... 546/251; 546/250
[58] Field of Search ................................ 546/250, 251

[56] References Cited

U.S. PATENT DOCUMENTS

| | | | |
|---|---|---|---|
| 3,428,034 | 11/1969 | Campbell et al. | 546/251 |
| 3,461,127 | 8/1969 | Colchester | 546/251 |
| 3,492,305 | 1/1970 | Colchester | 546/251 |
| 3,624,090 | 11/1971 | Clark et al. | 546/251 |

*Primary Examiner*—Robert T. Bond
*Attorney, Agent, or Firm*—John H. Shurtleff

[57] ABSTRACT

Pyridines are prepared by reacting a 2-alkoxy-2,3-dihydro-4H-pyran or a glutaraldehyde with ammonium nitrate in the presence of an aliphatic carboxylic acid and a catalytic amount of nitric acid.

The pyridines which can be prepared by the process according to the invention are useful starting materials for the preparation of dyes, drugs and pest control agents and are useful solvents.

10 Claims, No Drawings

PREPARATION OF PYRIDINES

The present invention relates to a novel process for the preparation of pyridines by reacting a 2-alkoxy-2,3-dihydro-4H-pyran or a glutaraldehyde with ammonium nitrate in the presence of an aliphatic carboxylic acid.

British Pat. No. 1,102,261 discloses a process for the preparation of pyridines by reacting glutaraldehyde, a substituted glutaraldehyde or a 2-alkoxy-2,3-dihydro-4H-pyran with ammonia or an ammonium salt in the presence of oxygen and a copper-II halide or iron-III halide. A pyridine selectivity of 44% is achieved, based on the dialdehyde employed. As well as the only moderate yield, the process has the disadvantage that 44 mole percent of copper-II chloride and 542 mole percent of ammonium chloride, based on aldehyde, are employed in the reaction, and this leads to by-products (chloropyridines), making isolation of the desired non-halogenated pryidine in the pure form difficult.

We have found that pyridines of the formula

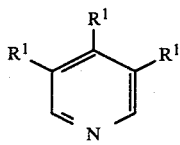

where the individual radicals $R^1$ are identical or different and each is hydrogen or an aliphatic radical, are obtained in an advantageous manner when (a) a 2-alkoxy-2,3-dihydro-4H-pyran of the formula

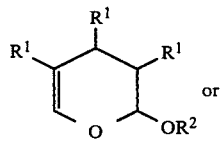

or (b) a glutaraldehyde of the formula

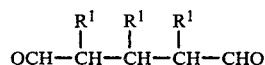

where $R^1$ has the above meanings and $R^2$ is an aliphatic radical, is reacted with ammonium nitrate in the presence of an aliphatic carboxylic acid, especially in the presence of a catalytic amount of nitric acid.

If 2,3-dihydro-2-methoxy-4H-pyran or glutaraldehyde is used, the reaction can be represented by the following equations:

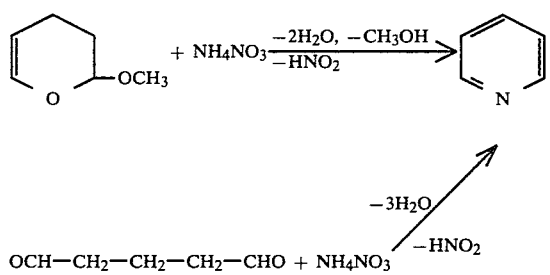

Compared with the conventional process, the process according to the invention gives pyridines in a better space/time yield, yield and purity in a simpler and more economical manner. Surprisingly, oxygen and/or other oxidants, such as salts of trivalent iron or manganese or of divalent copper, can be dispensed with, which results in a substantially simplified working up and isolation of the reaction product. The process is also particularly harmless to the environment, since no effluent-polluting heavy metal salts are required.

The starting material II or III can be reacted with ammonium nitrate in a stoichiometric amount or in excess, advantageously using from 1 to 2, in particular from 1 to 1.2, moles of ammonium nitrate per mole of starting material II or III. Preferred starting materials II and III and accordingly preferred end products I are those where the individual radicals $R^1$ and $R^2$ can be identical or different and each is alkyl of 1 to 4 carbon atoms; $R^1$ can also be hydrogen. The above radicals can also be substituted by groups which are inert under the reaction conditions, eg. alkyl or alkoxy each of 1 to 4 carbon atoms.

Examples of suitable starting materials II are thus, 2,3-dihydro-2-methoxy-4H-pyrans which are monosubstituted in the 3-, 4- or 5-position, disubstituted by identical or different substituents in the 3,4-, 4,5- or 3,5-position or trisubstituted by identical or different substituents in the 3,4,5-position, substituents being methyl, ethyl, propyl, isopropyl, butyl, isobutyl, sec.-butyl and tert.-butyl; and 2-ethoxy-, 2-propoxy-, 2-isopropoxy-, 2-butoxy-, 2-isobutoxy-, 2-sec.-butoxy- and 2-tert.-butoxy-4H-pyrans which are unsubstituted or homologously substituted by the above substituents.

Examples of suitable starting materials III are glutaraldehydes which are monosubstituted in the 2-, 3- or 4-position, disubstituted by identical or different substituents in the 2,3-, 3,4-, or 2,4-position or trisubstituted by identical or different substituents in the 2,3,4-position, substituents being methyl, ethyl, propyl, isopropyl, butyl, isobutyl, sec.-butyl and tert.-butyl; and unsubstituted glutaraldehyde.

The reaction is carried out in the presence of an aliphatic carboxylic acid as a solvent, advantageously with from 10 to 50, in particular from 15 to 30, moles of solvent per mole of starting material II or III. Examples of suitable acids are chloroacetic acid, acetic acid, propionic acid, butyric acid and isobutyric acid. The acids can be used in concentrated form or as mixtures with one another and/or with a solvent, in particular water. The acids as a rule contain not less than 2 carbon atoms. Acetic acid, propionic acid, butyric acid and isobutyric acid are preferred.

The reaction is generally carried out at from 50° to 150° C., preferably from 80° to 130° C. and in particular from 100° to 120° C., under atmospheric or superatmospheric pressure, continuously or batchwise. As a rule, no organic solvent is present, but water is advantageously used in an amount of from 50 to 200, in particular from 60 to 100, percent by weight, based on the starting material II or III.

In a preferred embodiment, in addition to the carboxylic acid, a catalytic amount of nitric acid is also 14 advantageously in the form of 20-60, in particular 40-50, percent strength by weight aqueous nitric acid, in an amount of from 0.001 to 0.1, in particular from 0.01 to 0.05, mole of nitric acid per mole of starting material II or III.

The reaction can be carried out as follows: a mixture of the starting material II or III and the aliphatic carboxylic acid, water, ammonium nitrate and nitric acid is added to the aliphatic carboxylic acid at the reaction temperature over a period of from 15 to 20 minutes. The end product is then isolated in a conventional manner, for example by distillation, addition of ammonia or sodium hydroxide solution, distillation or extraction, for example with ether, and distillation.

The pyridines I which can be prepared by the process according to the invention are useful starting materials for the preparation of dyes, drugs and pest control agents and are useful solvents. Regarding use of the products, reference may be made to the above publications and Ullmanns Encyklopädie der technischen Chemie, Volume 14, page 467.

In the Examples which follow, parts are by weight.

EXAMPLE 1

142 parts of 5-ethyl-2,3-dihydro-2-methoxy-4H-pyran are dissolved in 27 parts of water, 300 parts of acetic acid and 2 parts of 60 percent strength nitric acid at 22° C. After 15 minutes, a solution of 80 parts of ammonium nitrate in 80 parts of water is added. The resulting solution is run into 800 parts of acetic acid at 110° C. in the course of 20 minutes, while stirring. The reaction mixture is left to cool, the acetic acid and water are distilled off, 200 parts of water are added to the residue and the solution is rendered alkaline with 25 percent strength ammonia solution. The 3-ethylpyridine is extracted with ether. Distillation gives 91 parts (85% of theory) of 3-ethylpyridine of boiling point 60° C./15 mm Hg.

EXAMPLE 2

114 parts of 2,3-dihydro-2-methoxy-4H-pyran are dissolved in 27 parts of water, 300 parts of acetic acid and 2 parts of 60 percent strength nitric acid at 22° C. After 15 minutes, a solution of 80 parts of ammonium nitrate in 80 parts of water is added. The resulting solution is added to 800 parts of acetic acid at 110° C. in the course of 20 minutes, whilst stirring. The reaction mixture is cooled, the acetic acid and water are distilled off, 200 parts of water are added to the residue and the solution is rendered alkaline with 25 percent strength ammonia solution. The pyridine is extracted with ether. Distillation gives 58 parts (74% of theory) of pyridine of boiling point 115° C.

EXAMPLE 3

128 parts of 2-ethylglutaraldehyde, dissolved in 200 parts of acetic acid, and 88 parts of acetic acid, 88 parts of ammonium nitrate and 60 parts of water are run into 800 parts of acetic acid at from 110° to 115° C. in the course of 20 minutes. The reaction mixture is left to cool, the acetic acid and water are distilled off, 100 parts of water are added to the residue and the solution is rendered alkaline with 25 percent strength ammonia solution. The 3-ethylpyridine is extracted with ether. Distillation gives 93 parts (87% of theory) of 3-ethylpyridine of boiling point 60° C./15 mm Hg.

EXAMPLE 4

71 parts of 3-ethyl-2,3-dihydro-2-methoxy-4H-pyran are dissolved in 13 parts of water, 150 parts of propionic acid and 2 parts of 60 percent strength nitric acid at 22° C. After 15 minutes, this solution is run, simultaneously with 40 parts of ammonium nitrate in 30 parts of water, into 400 parts of propionic acid at from 120° to 140° C. in the course of 20 minutes. The reaction mixture is left to cool, the propionic acid, water and methanol are distilled off, 75 parts of water are added to the residue and the solution is rendered alkaline with 10 percent strength sodium hydroxide solution. The 3-ethylpyridine is extracted with ether. Distillation gives 35 parts (66% of theory) of 3-ethylpyridine of boiling point 60° C./15 mm Hg.

EXAMPLE 5

142 parts of 2,3-dihydro-2-methoxy-3,4-dimethyl-4H-pyran are dissolved in 25 parts of water, 300 parts of acetic acid and 2 parts of 60 percent strength nitric acid at 22° C. After 15 minutes, a solution of 80 parts of ammonium nitrate in 80 parts of water is added. The resulting solution is added to 800 parts of acetic acid at 110° C. in the course of 20 minutes, whilst stirring. The reaction mixture is cooled, the acetic acid, methanol and water are distilled off, 150 parts of water are added to the residue and the solution is rendered alkaline with 25 percent strength ammonia solution. The 3,4-dimethylpryidine is extracted with ether. Distillation gives 87 parts (81% of theory) of 3,4-dimethylpyridine of boiling point 68° C./15 mm Hg.

EXAMPLE 6

128 parts of 2,3-dihydro-2-methoxy-3-methyl-4H-pyran are dissolved in 25 parts of water, 250 parts of acetic acid and 2 parts of 60 percent strength nitric acid at 22° C. After 15 minutes, a solution of 80 parts of ammonium nitrate in 80 parts of water is added. The resulting solution is added to 800 parts of acetic acid at 110° C. in the course of 20 minutes, whilst stirring. The reaction mixture is cooled, the acetic acid, water and methanol are distilled off, 200 parts of water are added to the residue and the solution is rendered alkaline with 25 percent strength ammonia solution. The 3-methylpyridine is extracted with ether. Distillation gives 77 parts (83% of theory) of 3-methylpyridine of boiling point 143° C.

EXAMPLE 7

142 parts of 2-ethoxy-2,3-dihydro-4-methyl-4H-pyran are dissolved in 25 parts of water, 300 parts of acetic acid and 2 parts of 60 percent strength nitric acid at 22° C. After 15 minutes, a solution of 80 parts of ammonium nitrate in 80 parts of water is added. The resulting solution is added to 800 parts of acetic acid at 110° C. in the course of 20 minutes, whilst stirring. The reaction mixture is left to cool, the acetic acid, water and ethanol are distilled off, 200 parts of water are added to the residue and the solution is rendered alkaline with 25 percent strength ammonia solution. The 4-methylpyridine is extracted with ether. Distillation gives 73 parts (79% of theory) of 4-methylpyridine of boiling point 143° C.

EXAMPLE 8

142 parts of 2,3-dihydro-2-methoxy-3,5-dimethyl-4H-pyran are dissolved in 25 parts of water, 300 parts of acetic acid and 2 parts of 60 percent strength nitric acid at 22° C. After 15 minutes, a solution of 80 parts of ammonium nitrate in 80 parts of water is added. The resulting solution is run into 800 parts of acetic acid at 110° C. in the course of 20 minutes, whilst stirring. The reaction mixture is left to cool, the acetic acid, water and methanol are distilled off, 200 parts of water are added to the residue and the solution is rendered alkaline with 25 percent strength ammonia solution. The 3,5-dimethylpyridine is extracted with ether. Distillation gives 77 parts (72% of theory) of 3,5-dimethylpyridine of boiling point 172° C.

EXAMPLE 9

156 parts of 3-ethyl-2,3-dihydro-2-methoxy-5-methyl-4H-pyran are dissolved in 25 parts of water, 300 parts of acetic acid and 2 parts of 60 percent strength nitric acid at 22° C. After 15 minutes, a solution of 80 parts of ammonium nitrate in 80 parts of water is added. The resulting solution is added to 800 parts of acetic acid at 110° C. in the course of 20 minutes, whilst stirring. The reaction mixture is left to cool, the acetic acid, water and methanol are distilled off, 200 parts of water are added to the residue and the solution is rendered alkaline with 25 percent strength ammonia solution. The 3-ethyl-5-methyl-pyridine is extracted with ether. Distillation gives 80 parts (66% of theory) of 3-ethyl-5-methyl-pyridine of boiling point 83° C./15 mm Hg.

EXAMPLE 10

170 parts of 3,5-diethyl-2,3-dihydro-2-methoxy-4H-pyran are dissolved in 25 parts of water, 300 parts of acetic acid and 2 parts of 60 percent strength nitric acid at 22° C. After 15 minutes, a solution of 88 parts of ammonium nitrate in 80 parts of water is added. The resulting solution is run into 800 parts of acetic acid at 110° C. in the course of 20 minutes, whilst stirring. The reaction mixture is left to cool, the acetic acid, water and methanol are distilled off, 200 parts of water are added to the residue and the solution is rendered alkaline with 25 percent strength ammonia solution. The 3,5-diethylpyridine is extracted with ether. Distillation gives 87 parts (64% of theory) of 3,5-diethylpyridine of boiling point 92° C./15 mm Hg.

We claim:

1. A process for the preparation of a pyridine of the formula

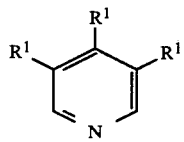

where the individual radicals $R^1$ are identical or different and each is hydrogen or an alkyl of 1 to 4 carbon atoms, which process comprises reacting (a) a 2-alkoxy-2,3-dihydro-4H-pyran of the formula

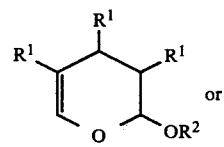

(b) a glutaraldehyde of the formula

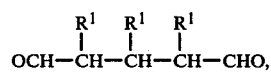

where $R^1$ has the above meanings and $R^2$ is an alkyl of 1 to 4 carbon atoms, with ammonium nitrate in the presence of an aliphatic carboxylic acid and a catalytic amount of nitric acid.

2. A process as claimed in claim 1, wherein the reaction is carried out with from 1 to 2 moles of ammonium nitrate per mole of starting material II or III.

3. A process as claimed in claim 1, wherein the reaction is carried out in the presence of an aliphatic carboxylic acid, as the solvent, in an amount of from 10 to 50 moles per mole of starting material II or III.

4. A process as claimed in claim 1, wherein the reaction is carried out at from 50° to 150° C.

5. A process as claimed in claim 1, wherein the reaction is carried out at from 80° to 130° C.

6. A process as claimed in claim 1, wherein the reaction is carried out with from 50 to 200 percent by weight of water, based on the starting material II or III.

7. A process as claimed in claim 1, wherein the reaction is carried out with nitric acid in the form of from 20 to 60 percent strength by weight aqueous nitric acid, in an amount of from 0.001 to 0.1 mole of nitric acid per mole of starting material II or III.

8. A process as claimed in claim 1 wherein the aliphatic carboxylic acid is selected from the group consisting of acetic acid, propionic acid, butyric acid and isobutyric acid.

9. A process as claimed in claim 8 wherein the reaction is carried out with
   (a) from 1 to 2 moles of ammonium nitrate per mole of starting material II or III,
   (b) from 10 to 50 moles of the aliphatic carboxylic acid, as a solvent, per mole of the starting material II or III,
   (c) from 50 to 200 percent by weight of water, based on the starting material II or III, and
   (d) from 0.001 to 0.1 mole of nitric acid, in the form of from 20 to 60 percent strength by weight of aqueous nitric acid, per mole of the starting material II or III.

10. A process as claimed in claim 9 wherein the reaction is carried out at from 80° to 130° C.

* * * * *